(12) United States Patent
Bullen et al.

(10) Patent No.: US 9,150,469 B2
(45) Date of Patent: Oct. 6, 2015

(54) AROMATIC ALKYLATION PROCESS WITH REDUCED BYPRODUCT FORMATION

(75) Inventors: Patrick J. Bullen, Elmhurst, IL (US);
Steven P. Lankton, Wheeling, IL (US);
Robert J. Schmidt, Barrington, IL (US)

(73) Assignee: UOP LLC, Des Plaines, IL (US)

( * ) Notice: Subject to any disclaimer, the term of this patent is extended or adjusted under 35 U.S.C. 154(b) by 1126 days.

(21) Appl. No.: 12/467,622

(22) Filed: May 18, 2009

(65) Prior Publication Data

US 2010/0292519 A1    Nov. 18, 2010

(51) Int. Cl.
*C07C 2/00* (2006.01)
*C07C 6/12* (2006.01)
*C07C 7/148* (2006.01)

(52) U.S. Cl.
CPC .............. *C07C 6/126* (2013.01); *C07C 7/1485* (2013.01); *C07C 2521/04* (2013.01); *C07C 2521/08* (2013.01); *C07C 2529/08* (2013.01); *C07C 2529/70* (2013.01)

(58) Field of Classification Search
USPC ......... 585/300, 304, 449, 450, 470, 400, 314, 585/316, 323, 467, 475, 804; 203/2, 4, 94, 203/98, 99
See application file for complete search history.

(56) References Cited

U.S. PATENT DOCUMENTS

| | | | | |
|---|---|---|---|---|
| 3,927,134 A * | 12/1975 | Yanagihara et al. | ........... | 585/314 |
| 4,169,111 A * | 9/1979 | Wight | ............................ | 585/323 |
| 4,347,393 A | 8/1982 | Miki | .............................. | 585/323 |
| 4,774,377 A | 9/1988 | Barger et al. | ................. | 585/323 |
| 4,891,458 A * | 1/1990 | Innes et al. | ...................... | 585/323 |
| 4,950,834 A * | 8/1990 | Arganbright et al. | ......... | 585/446 |
| 5,003,119 A * | 3/1991 | Sardina et al. | .................. | 585/323 |
| 5,955,642 A * | 9/1999 | Merrill et al. | ................. | 585/323 |
| 6,034,291 A | 3/2000 | Girotti et al. | ................... | 585/323 |
| 6,936,744 B1 * | 8/2005 | Cheng et al. | ................... | 585/475 |
| 7,202,390 B2 | 4/2007 | Bokade et al. | ................. | 585/467 |
| 7,371,910 B2 | 5/2008 | Yeh et al. | ....................... | 585/467 |
| 7,420,098 B2 | 9/2008 | Schmidt | ......................... | 585/449 |
| 2008/0194890 A1 | 8/2008 | Brown | ............................. | 585/16 |
| 2008/0194897 A1 | 8/2008 | Clark et al. | ..................... | 585/455 |

FOREIGN PATENT DOCUMENTS

| | | | | |
|---|---|---|---|---|
| EP | 0537389 A1 | 4/1993 | ................ | C07C 2/66 |
| WO | 8912613 | 12/1989 | ................ | C07C 6/12 |

OTHER PUBLICATIONS

Schmidt, Robert J. et al., "New catalyst innovations for cumene alkylation," Research and Development, UOP LLC, Des Plaines, IL AIChE Spring National Meeting,—Tampa, Florida, Apr. 26-30, 2009.

(Continued)

*Primary Examiner* — In Suk Bullock
*Assistant Examiner* — Sharon Pregler

(57) ABSTRACT

Byproduct formation in aromatic alkylation processes is reduced when different polyalkylated aromatic compounds are first fractionated into separate streams enriched in these respective polyalkylated aromatic compounds, and the separate streams are sent to different transalkylation reaction zones, which may or may not be in the same reactor. The different transalkylation reaction zones allow for greater control of the transalkylation of the respective polyalkylated aromatic compounds, such as diisopropylbenzene (DIPB) and triisopropylbenzene (TIPB) that accompany the alkylation of benzene with propylene in a process for cumene production.

16 Claims, 2 Drawing Sheets

(56) References Cited

OTHER PUBLICATIONS

Canfield, R. et al., "Improving cumene yields via selective catalysis," *Chem. Eng. (N.Y.)* (ISSN 0009-2460) v 90 n 6 (Mar. 21, 1983) p. 32-33.

Mita, Y. et al., "Up cumene yield with transalkylation," *Hydrocarbon Process*, v 47 n 10 (Oct. 1968) Gulf Publishing Co. p. 122-24.

Canfield, R. et al., "The new cumene process efficient and economical,".

"New Monsanto/lummus crest cumene process technology," Monsanto Co., Lummus Crest Europe, Rhone Poulenc Chimie de Base, *Pet., Inf. Int.* (ISSN 0755-561X) n 1617 29 (Nov. 1985) Societe d'Information et de Documentation; Bureau d'Informations Professionelles (French) [Abstract].

Schulz, R. et al., "Cumene technology improvement," UOP LLC, 1988 *AIChE Summer Natl. Meeting*, (Denver Aug. 21-24, 1988) Prepr. N 79f pp. 1-19.

"HP Innovations—highly selective cumene process," Flor Daniel GTI, *Hydrocarbon Processing*, Oct. 1996, p. 40-41.

Ohnuma, H. et al., "Transalkylation of aromatic hydrocarbons (II) reaction between di-*iso*-propylbenzene and benzene," *Sekiyu Gakkai Shi*, v 11 n 6 443-447. (1968) [Abstract].

\* cited by examiner

AROMATIC ALKYLATION PROCESS WITH REDUCED BYPRODUCT FORMATION

FIELD OF THE INVENTION

The present invention relates to methods for transalkylating hydrocarbon feed streams, and particularly those containing two or more polyalkylated aromatic compounds obtained from the production of monoalkylated aromatic compounds such as cumene and ethylbenzene, in aromatic alkylation processes.

DESCRIPTION OF RELATED ART

The alkylation of aromatic substrates with olefins to produce monoalkyl aromatics is a well developed art that is practiced industrially on a large scale. One commercial application is the alkylation of benzene with propylene to produce cumene (isopropylbenzene), which is subsequently used in the manufacture of phenol and acetone via the air oxidation of cumene and subsequent acid-catalyzed decomposition of the intermediate hydroperoxide. Another commercial application is the alkylation of benzene with ethylene to produce ethylbenzene, which is often subsequently dehydrogenated in the manufacture of styrene monomer. In the endothermic dehydrogenation reaction, steam is normally used to provide the required sensible heat. The general design and operation of aromatic alkylation processes are known.

In these aromatic alkylation processes, as the molar ratio of aromatic substrate (e.g., benzene) per olefinic alkylation agent (e.g., propylene) increases, currently available catalysts typically exhibit improved selectivity to the desired monoalkylated aromatic compound (e.g., cumene). However, even at a high molar ratio of aromatic substrate per olefin, dialkylated aromatic compounds (e.g., diisopropylbenzene, DIPB) and trialkylated aromatic compounds (e.g., triisopropylbenzene, TIPB) accompany the production of the desired monoalkylated aromatic compound. While these polyalkylated aromatic compounds represent a reduction in the efficient use of the aromatic substrate and olefin in the alkylation reaction zone, they are normally readily transalkylated in a separate transalkylation reaction zone, with the same aromatic substrate as used in the alkylation zone, in the presence of a suitable transalkylation catalyst. Transalkylation thereby effectively produces an additional amount of the desired monoalkylated aromatic compound, using as transalkylation agents the polyalkylated aromatic products of aromatic alkylation, as discussed above. The so-called combination processes, involving both alkylation and transalkylation, can therefore significantly improve monoalkylated aromatic compound production.

In such alkylation zone/transalkylation zone combination processes, the aromatic substrate (e.g., benzene) is normally used in stoichiometric excess in both reaction zones. A common way for reducing the substantial expense of removing and recycling the unreacted benzene or other aromatic substrate in the respective reaction zone effluents involves passing them (optionally after removing light components such as propane from one or both effluents by fractionation) to a common product separation section. The same distillation columns and other equipment can therefore be used to recover unreacted aromatic substrate from the combined alkylation and transalkylation effluent streams and recycle portions of the recovered aromatic substrate back to both of these reaction zones. In addition to recovery of the aromatic substrate, another important function of the distillation columns in the product separation section is the recovery of polyalkylated aromatic compounds, and particularly di- and trialkylated aromatic compounds, as discussed above, for use as transalkylation agents in the transalkylation reaction zone. Heavier polyalkylated aromatic products as well as other higher boiling byproducts of either reaction zone, such as diphenylalkanes, are normally collectively removed in the bottoms stream of a distillation column (e.g., a polyisopropylbenzene column or a polyethylbenzene column, which recovers lighter, di- and trialkylated aromatic compounds in an overhead or a lower boiling fraction). The feed to this distillation column is normally a hydrocarbon feed stream obtained from distillation to recover the desired monoalkylated aromatic product as an overhead or a lower boiling fraction.

In a representative aromatic alkylation process for producing the monoalkylated aromatic compound cumene, for example, liquid benzene and liquid propylene are charged into an alkylation reaction zone comprising one or more reactors containing alkylation catalyst. In order to minimize the production of polyalkylated benzene compounds, a molar excess of benzene to propylene, for example in the range from about 4:1 to about 16:1, is normally maintained throughout the alkylation reaction zone. The effluent from this reaction zone is generally sent to a depropanizer column for the removal, by distillation, of lower boiling components such as propane and water that may be present initially in the propylene feed. The depropanizer column bottoms is then combined with the effluent from the transalkylation reaction zone comprising a transalkylation catalyst. As discussed above, non-selective polyalkylated aromatic products of the alkylation reaction, namely DIPB and TIPB, are reacted with benzene in the transalkylation reaction zone to produce additional monoalkylated aromatic product, in this case cumene.

In this representative cumene production process, the combined alkylation and transalkylation reaction zone effluents (optionally after removal of low boiling components, for example the removal of propane from the alkylation reaction zone effluent) are therefore sent to the same product separation section to recover benzene, cumene product, polyisopropylbenzene byproducts of the alkylation reaction zone (e.g., DIPB and TIPB), and heavier byproducts by distillation. Traditionally, three distillation columns are used for product separation. The first is normally termed a benzene column, used to recover excess benzene from the reactor effluents in an overhead or lower boiling fraction. The recovered benzene is then recycled to the alkylation and transalkylation zones to satisfy some or all of the benzene needed to obtain the desired benzene:olefin ratio in each zone. The second distillation column is normally termed a cumene column, the feed to which is generally the bottoms or a higher boiling fraction of the upstream benzene column. The cumene product is often taken as a net overhead or low boiling faction from the cumene column. The cumene product may then be used in downstream applications such as phenol or acetone production processes, or otherwise may be sent to storage. The third distillation column is normally termed a polyisopropylbenzene column, the feed to which is generally the bottoms or a higher boiling fraction of the upstream cumene column. As discussed above, the polyisopropylbenzene column is used to recover lighter, mono- and di-alkylated aromatic compounds in an overhead or lower boiling fraction and recycle these to the transalkylation reaction zone. Heavier polyalkylated aromatic products as well as other byproducts of either reaction zone, such as diphenylalkanes, are normally removed in the bottoms stream or higher boiling fraction of the polyisopropylbenzene column. The collective heavy ends may be cooled and sent to storage.

In any aromatic alkylation process, the overriding objectives, which govern process economics, are achieving a high conversion of the olefinic alkylation agent (which is normally the limiting reagent) and a high selectivity to the desired monoalkylated aromatic product. These objectives, relating to improving the product yield and product purity, are addressed by limiting the overall production of byproducts in the combination processes described above. Various alkylaromatic production processes and catalysts used in these processes, along with their associated advantages are described, for example, in U.S. Pat. Nos. 7,498,471; 6,440,886; 6,339,179; and US 2008/0171902. Improvements that relate to reducing byproduct formation in the production of alkylated aromatic hydrocarbons such as cumene and ethylbenzene are continually being sought. Those skilled in the art recognize the significant commercial impact of even modest improvements in product yields and/or product quality.

SUMMARY OF THE INVENTION

The present invention is associated with the finding that overall byproduct formation in aromatic alkylation processes can be reduced when different polyalkylated aromatic compounds are first fractionated into separate streams enriched in these respective polyalkylated aromatic compounds and then sent to different transalkylation reaction zones, which may or may not be in the same reactor. This allows the catalysts and/or reaction conditions in these transalkylation reaction zones to be better tailored to a specific feedstock (i.e., enriched in a specific polyalkylated aromatic compound), such that conversion can be increased and/or byproduct production reduced. The overall yield (conversion times selectivity) of the desired monoalkylated aromatic is thereby increased. Product purity may also be increased if byproducts that are difficult to separate from (e.g., are similar in volatility to) the main product are reduced.

In the case of an aromatic alkylation process for producing cumene (isopropylbenzene) from propylene and benzene, for example, both the alkylation and transalkylation reactions produce byproduct ethylbenzene (EB). Due to its boiling point being close to that of cumene, EB is not easily separated from this desired monoalkylated product by distillation. The commercial demand for cumene having a low ethylbenzene content is therefore not easily satisfied without incurring higher capital and/or utility costs associated with the construction and operation of conventional alkylation/transalkylation cumene production plants.

According to embodiments of the present invention, the production of byproduct EB is reduced by fractionating di- and tri-alkylated aromatic products of benzene alkylation with propylene, namely diisopropylbenzene and triisopropylbenzene (DIPB and TIPB), into separate streams enriched in DIPB and TIPB, respectively. These streams are then sent to separate transalkylation reaction zones where reaction of these polyalkylated aromatic transalkylation agents with benzene produces an additional amount of the desired cumene product. The separate transalkylation reaction zones can comprise different transalkylation catalysts, different amounts or proportions of the same catalysts, and/or different operating conditions in order to better match a particular polyalkylated aromatic to a particular transalkylation reaction zone catalyst and/or set of operating conditions, thereby reducing the formation of byproduct EB and/or other byproducts and improving reaction selectivity to the desired monoalkylated aromatic compound cumene.

In an analogous manner, diethylbenzene and triethylbenzene products of benzene alkylation with ethylene can be fractionated into separate streams enriched in these products and sent to different transalkylation zones to reduce overall byproduct formation in ethylbenzene production from the alkylation of benzene with ethylene. In processes for either cumene or ethylbenzene production, the hydrocarbon feed streams that are fractionated into separate transalkylation feed streams, enriched in respective polyalkylated aromatic compounds, are generally obtained in the product separation sections of these processes. In particular, the hydrocarbon feed streams can be obtained as a bottoms or higher boiling fraction from distillation to recover the cumene product stream or the ethylbenzene product stream in an overhead or lower boiling fraction. For example, the hydrocarbon feed stream can be the cumene column bottoms stream in the representative cumene production process as discussed above. Likewise, the hydrocarbon feed stream can be an ethylbenzene column bottoms stream from the product separation section of a representative ethylbenzene production process.

These and other aspects and features relating to the present invention are apparent from the following Detailed Description.

Figure 1:
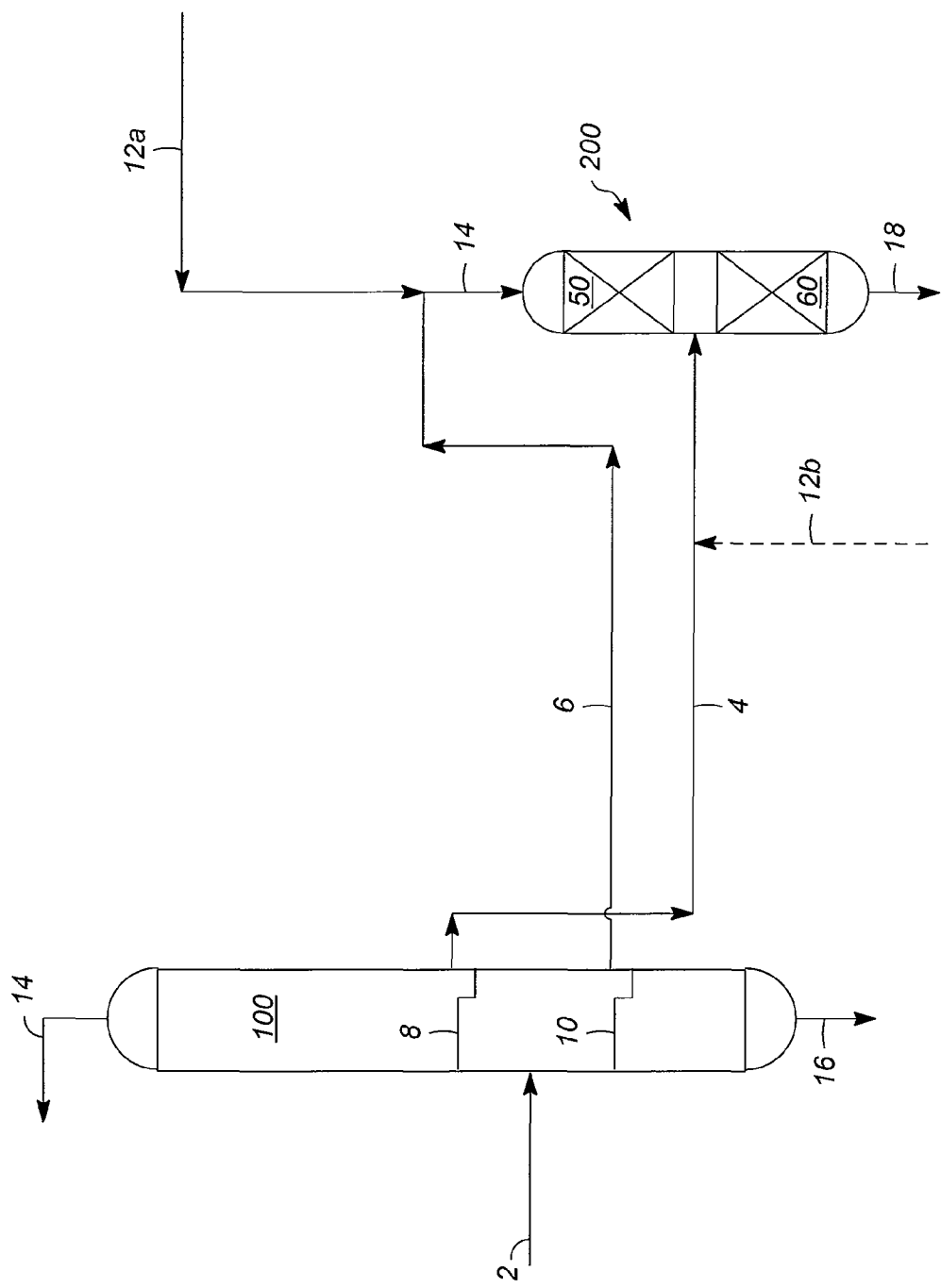
FIG. 1 depicts a transalkylation section of a representative cumene production process, in which transalkylation feed streams enriched in different polyalkylated aromatic transalkylation agents, namely DIPB and TIPB, are separated using distillation and fed to different transalkylation reaction zones within a common reactor.

The same reference numbers are used to illustrate the same or similar features throughout the drawings. The drawings are to be understood to present an illustration of the invention and/or principles involved. Details including pumps, compressors, instrumentation, and other items not essential to the understanding of the invention are not shown. As is readily apparent to one of skill in the art having knowledge of the present disclosure, methods for transalkylating polyalkylated aromatics as described herein, and particularly those that are integrated into combination alkylation zone/transalkylation zone processes (e.g., as described above for the production of cumene or ethylbenzene), according to various other embodiments of the invention, will have configurations and components determined, in part, by their specific use.

DETAILED DESCRIPTION

In aromatic alkylation processes such as the combined alkylation zone/transalkylation zone processes described above and used in the production of cumene or ethylbenzene, benzene is the aromatic alkylation substrate of principal interest, but alkyl-substituted benzenes may be used. Also, more than one aromatic alkylation substrate may be used. Monoolefins are principally used as the olefinic alkylation agent, but diolefins, polyolefins, acetylene hydrocarbons, and substituted hydrocarbons can be used. The olefinic alkylation agent preferably contains 2 or 3 carbon atoms, but olefins having from 2 to 20 carbon atoms may be used. Propylene and ethylene are the preferred olefinic alkylating agents, and these are used, respectively, in the aromatic alkylation processes for the production of cumene and ethylbenzene, respectively. More than one olefinic alkylation agent may be used.

The polyalkylated aromatic transalkylation agents, which accompany the production of the desired monoalkylated aromatic compound, transalkylate with the alkylation substrate to produce an additional amount of this desired product. The transalkylation agents may be introduced from a source that is not part of the overall, combined alkylation zone/transalkylation zone process, but more commonly the transalkylation agents are recovered in the product separation section of the combined process. Dialkyl benzenes (e.g., DIPB and diethylbenzene) and trialkyl benzenes (e.g., TIPB and triethylbenzene) are the principal polyalkylated aromatic transalkylation agents in processes for producing monoalkylated benzenes (e.g., cumene and ethylbenzene) as the desired products. However, the desired alkylated aromatic compound may in some cases itself be polyalkylated. As the number of alkyl groups on the desired alkylated aromatic product increases, it will be appreciated that the number of alkyl groups on the polyalkylated aromatic transalkylation agents correspondingly increase. In any event, the desired alkylated aromatic product has at least one more alkyl group than the aromatic alkylation substrate and at least one less alkyl group that the polyalkylated aromatic transalkylation agent.

Figure 2:
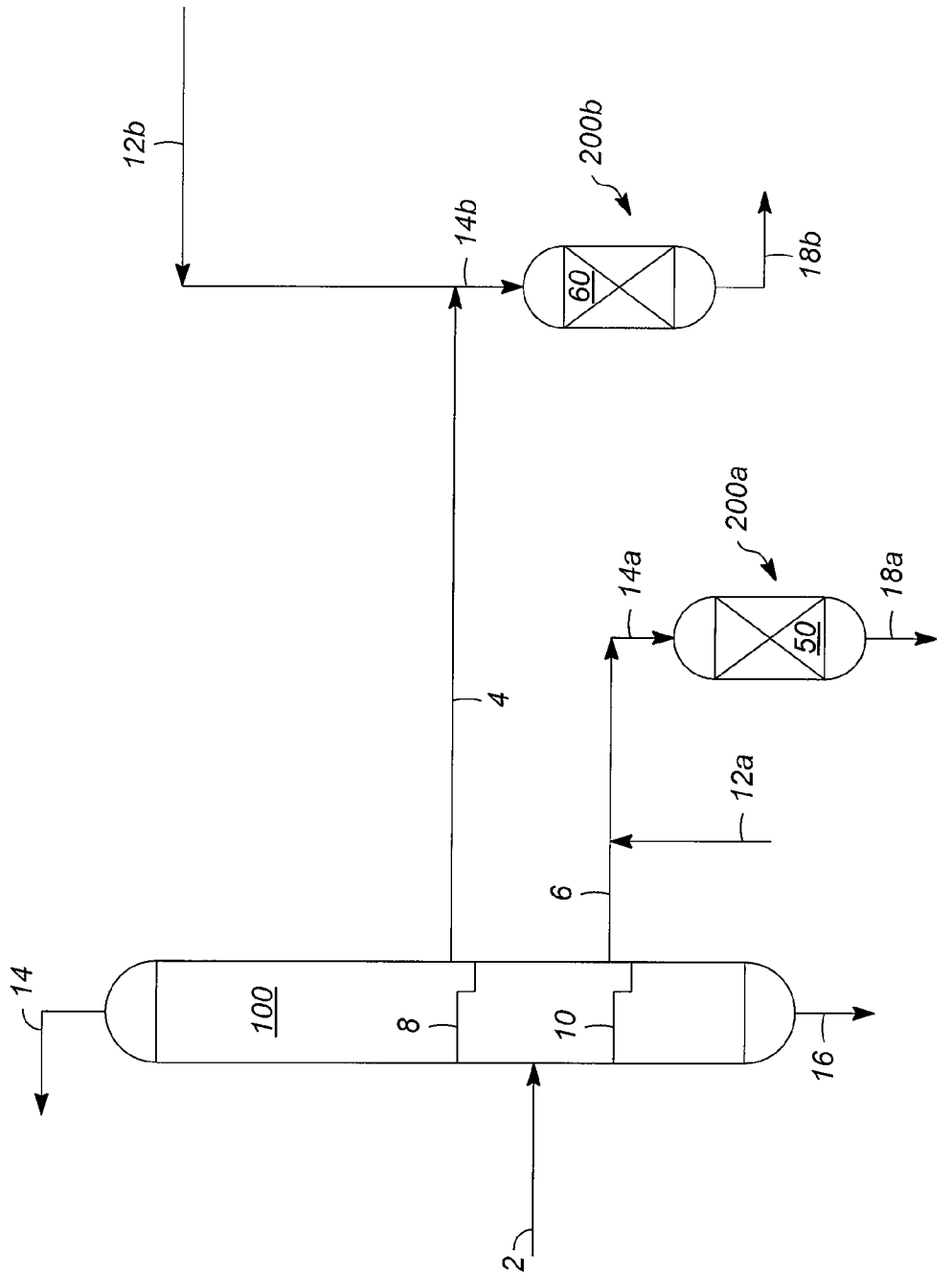
FIG. 2 depicts an alternative embodiment in which the separated transalkylation feed streams enriched in DIPB and TIPB are fed to different transalkylation reaction zones within separate reactors.

As discussed above, widely practiced hydrocarbon conversion processes to which the present invention is applicable are (1) the production of cumene by alkylation of benzene with propylene and by transalkylation of benzene with polyisopropylbenzenes (e.g., DIPB and TIPB) that accompany benzene alkylation, and (2) the production of ethylbenzene by alkylation of benzene with ethylene and by transalkylation of benzene with polyethylbenzenes (e.g., diethylbenzene and triethylbenzene) that accompany benzene alkylation. Cumene production is an exemplary process used to further illustrate the invention, particularly with respect to the preferred embodiments of the invention shown in FIGS. 1 and 2. As these illustrative methods are for transalkylation of hydrocarbon feed streams comprising first and second aromatic transalkylation agents, it is understood that they may be readily integrated into combination alkylation zone/transalkylation zone processes described above for either cumene or ethylbenzene. Also, while the embodiments of FIGS. 1 and 2 illustrate the separation of a hydrocarbon feed stream into two transalkylation feed streams, it will be appreciated that more than two separate feed streams having different compositions (e.g., enriched in different polyalkylated aromatic compounds) may be also be provided without departing from the scope of the present invention.

Embodiments of the invention are therefore broadly directed to methods for transalkylating a hydrocarbon feed stream comprising first and second polyalkylated aromatic transalkylation agents. The methods comprise (a) separating the hydrocarbon feed stream to provide a first transalkylation feed stream enriched in the first polyalkylated aromatic transalkylation agent and a second transalkylation feed stream enriched in the second polyalkylated aromatic transalkylation agent and (b) passing the first and second transalkylation feed streams into different transalkylation reaction zones. The characteristic of each of the transalkylation feed stream being enriched in a given polyalkylated aromatic transalkylation agent is in reference to the amount of that agent in the hydrocarbon feed stream. Typically, the separate transalkylation feed streams are enriched in components (i.e., the first or second polyalkylated transalkylation agents) using a distillation column such as the polyisopropylbenzene column described above with respect to a representative cumene production process. The feed to this polyisopropylbenzene column is normally the bottoms or a high boiling fraction of the upstream cumene column. Likewise, a polyethylbenzene column, the feed to which is normally the bottoms or a high boiling fraction of an upstream ethylbenzene column in an ethylbenzene production process, may be used to provide fractions enriched in diethylbenzene and triethylbenzene as first and second polyalkylated aromatic transalkylation agents. In a preferred embodiment, the separated, first and second transalkylation feed streams are taken as side draws at appropriate stages from these respective distillation columns in the product separation sections of cumene or ethylbenzene production processes. For example, the transalkylation feed stream enriched in a lower boiling, dialkylated aromatic compound (e.g., DIPB or diethylbenzene) may be removed as a side draw at a stage above that from which the transalkylation feed stream enriched in a higher boiling, trialkylated aromatic compound (e.g., TIPB or triethylbenzene) is removed.

The different transalkylation reaction zones require that the first and second transalkylation feed streams are exposed to different reaction conditions and/or catalyst beds. For example, these zones may be in a common reactor, which is fed by the separated transalkylation feed streams at different locations along the reactor length (e.g., into different catalyst beds, which may or may not comprise the same catalyst, in upper and lower reactor sections), whereby the upstream feed contacts the same catalyst bed as the downstream feed, after passing over an upstream catalyst bed. Alternatively, the different transalkylation reaction zones may be in separate reactors, such that the first and second transalkylation feed streams do not contact the same catalyst bed (which may or may not comprise the same catalyst).

In general, but not necessarily, the different transalkylation feed streams that are separated (e.g., by distillation) are passed to the inlets of catalyst beds comprising different types of catalysts. The catalysts used for transalkylation generally comprise one of a class of aluminosilicate molecular sieves known as zeolites. The zeolitic molecular sieves suitable for use in zeolitic transalkylation catalysts are crystalline aluminosilicates which in the calcined form may be represented by the general formula:

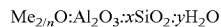

$$Me_{2/n}O:Al_2O_3:xSiO_2:yH_2O$$

where Me is a cation, n is the valence of the cation, x has a value of from about 5 to 100, and y has a value of from about 2 to 10. Zeolites are described in detail by D. W. Breck, *Zeolite Molecular Sieves*, John Wiley and Sons, New York (1974), and elsewhere. Suitable zeolites include Y zeolite, beta zeolite, X zeolite, mordenite, faujasite, zeolite omega, UZM-8, ZSM-5, PSH-3, MCM-22, MCM-36, MCM-49, and MCM-56. One or more types of zeolitic transalkylation catalyst may be used in catalyst beds of different transalkylation reaction zones to which the different transalkylation feed streams are passed. The use of different zeolitic transalkylation catalysts is associated with one representative embodiment of the invention for tailoring first and second transalkylation feed streams (e.g., enriched in different polyalkylated aromatic compounds such as DIPB and TIPB) to particular reaction zones (or reaction environments) to reduce byproduct formation.

A type of Y zeolite for use as a transalkylation catalyst has a non-$H^+$ cation content of the zeolite Y of less than 200 ppm by weight, calculated as $NH_3$ equivalents. Beta zeolite is described in U.S. Pat. Nos. 4,891,458 and 5,081,323. Surface-modified beta zeolite, as described in U.S. Pat. No. 5,723,710, is an exemplary beta zeolite suitable as a transalkylation catalyst. In any zeolitic transalkylation catalyst, the zeolite is generally present in an amount of at least 50% by weight, and often in an amount of at least 90% by weight, of the total catalyst weight, with the balance in most cases being a refractory inorganic oxide binder. A preferred binder is alumina, with gamma-alumina, eta-alumina, and mixtures thereof being particularly preferred. A representative zeolitic transalkylation catalyst comprises Y zeolite and an alumina or silica binder. Another comprises beta zeolite and an alumina or silica binder. In general, the zeolites described above are also suitable for use as alkylation catalysts in combination alkylation zone/transalkylation zone processes as described above.

In a preferred embodiment of the invention associated with a combination alkylation zone/transalkylation zone process for the production of cumene, a transalkylation feed stream enriched in TIPB is fed to a transalkylation reaction zone comprising a zeolitic transalkylation catalyst comprising Y zeolite. A preferred Y zeolite is a modified Y zeolite known as Y-85 and described in US 2008/0171902, hereby incorporated by reference. Also, it is preferred that a transalkylation feed stream enriched in DIPB is fed to a transalkylation reaction zone comprising a zeolitic transalkylation catalyst comprising beta zeolite. Advantageously, the formation of byproduct ethylbenzene is very small over beta zeolite, and is essentially in proportion to the overall conversion of DIPB to the desired product cumene.

In a particular embodiment in which the feed stream enriched in TIPB is fed to a zeolitic catalyst bed upstream of a second zeolitic catalyst bed comprising beta zeolite, to which the feed stream enriched in DIPB is fed (e.g., in the case of the DIPB-enriched feed stream being fed at an interbed addition point between separate beds of catalyst comprising Y zeolite and beta zeolite in a stacked bed reactor), the byproduct ethylbenzene formation will be essentially in proportion to the total conversion of DIPB and TIPB by transalkylation. Embodiments of the invention therefore reduce byproduct formation, and particularly ethylbenzene, by separating the relatively minor portion of TIPB (typically representing only from about 3% to about 10% by weight of the hydrocarbon feed stream comprising both DIPB and TIPB) and feeding this minor portion over a bed of catalyst comprising Y zeolite, which provides a high conversion of TIPB but an overall low contribution of byproduct ethylbenzene due to the relatively low mass flow rate of the TIPB-enriched feed stream. In this manner, the use of different transalkylation reaction zones (e.g., having different transalkylation reaction conditions and/or comprising different catalyst beds), allows increased conversion of polyalkylated aromatic transalkylation agents with reduced byproduct formation.

The effluent(s) from the transalkylation reaction zones are, relative to each of the respective transalkylation feed streams, enriched in the desired alkylaromatic product (e.g., a monoalkylated aromatic such as cumene or ethylbenzene) as a result of reactions between the polyalkylated transalkylation agents and the aromatic substrate (e.g., benzene). The transalkylation reaction zone effluents may then be combined with an alkylation reaction zone effluent, optionally after removal of light components such as propane and/or water from this alkylation reaction zone effluent using distillation. The alkylation reaction zone effluent and transalkylation reaction zone effluent(s) may be combined prior to or during distillation to enrich a lower boiling fraction in the aromatic alkylation substrate used in both the alkylation and transalkylation reaction zones. For example, these alkylation and transalkylation reaction zone effluents may be combined upstream of a benzene column used to remove unreacted benzene as an overhead or lower boiling fraction as discussed above.

The first and second transalkylation feed streams, in an overall process for cumene production, may be enriched in DIPB and TIPB as transalkylation agents, respectively. In an overall process for ethylbenzene production, the first and second transalkylation feed streams may be enriched in diethylbenzene and triethylbenzene, respectively. In a representative embodiment, therefore, the number of alkyl groups of the second polyalkylated aromatic transalkylation agent exceeds the number of alkyl groups of the first polyalkylated aromatic transalkylation agent by one. The hydrocarbon feed stream that is separated to provide the first and second transalkylation feed streams will normally comprise less than about 15% by weight (e.g., from about 3% to about 10% by weight), and often less than about 5% by weight, of the higher boiling, second polyalkylated aromatic transalkylation agent (e.g., triisopropylbenzene).

In the case of either a cumene production process or an ethylbenzene production process (e.g., an alkylation zone/transalkylation zone combination process as described above), the hydrocarbon feed stream containing both the first and second polyalkylated aromatic transalkylation agents normally comprises a process stream of the product separation sections (downstream of the alkylation and transalkylation reaction zones) of these respective aromatic alkylation processes. In a cumene production process or an ethylbenzene production process, for example, the hydrocarbon feed stream may be the bottoms from a cumene column or an ethylbenzene column, respectively. These distillation columns are typically used to recover, respectively, a cumene product stream or an ethylbenzene product stream as a net overhead liquid (i.e., after returning a reflux portion) or lower boiling fraction.

In the illustrative embodiment shown in FIG. 1, a hydrocarbon feed stream 2 comprising both of the polyalkylated aromatic transalkylation agents, namely DIPB and TIPB, is transalkylated according to methods of the present invention. Hydrocarbon feed stream 2 may be obtained as the bottoms product of an upstream cumene column (not shown) used in the product separation section of a cumene production process. The cumene column is generally used is such processes to recover the cumene product stream as a net overhead product. As discussed above, hydrocarbon feed stream 2 will typically contain from about 3% to about 10% by weight of the TIPB, with the balance being substantially DIPB. Smaller amounts of higher boiling components (collectively referred to as heavy hydrocarbons or heavy ends) and lower boiling components and may be removed as bottoms stream 16 and overhead stream 14 and from diisopropylbenzene column 100, respectively.

The diisopropylbenzene column 100 is used to fractionate the hydrocarbon feed stream 2 to provide two separate transalkylation feed streams 4, 6, which are enriched in DIPB and TIPB, respectively. These first and second, separate transalkylation feed streams 4, 6, as shown, may be taken as side draws from diisopropylbenzene column 100, with the second feed stream 6 enriched in the higher boiling polyalkylated aromatic, TIPB, being removed at a lower stage 10 of diisopropylbenzene column 100, relative to the stage 8 at which the first feed stream 4 enriched in the lower boiling polyalkylated aromatic, DIPB, is withdrawn.

As illustrated in the embodiment shown in FIG. 1, a benzene stream 12a and the second transalkylation feed stream 6 enriched in TIPB are fed to the top of transalkylation reactor 200, which contains two beds 50, 60 of separate, first and second zeolitic catalysts. After transalkylation feed stream 6 and benzene stream 12a are combined, the resulting combined feed stream 14 flows downwardly through transalkylation reactor 200, contacting both beds 50, 60 of zeolitic catalyst. As depicted in FIG. 1, therefore, transalkylation reactor

200 is a two-bed downflow type reactor with an interbed addition point for transalkylation feed stream 4, enriched in DIPB. In the combined feed stream 14, the benzene:TIPB molar ratio is preferably in the range from about 5:1 to 1000:1 at the inlet of transalkylation reactor 200, which is located at the top of this reactor in the embodiment of FIG. 1. The temperature of the combined feed stream 14 at the inlet of this reactor is preferably from about 100° C. (212° F.) to about 200° C. (392° F.). The combined feed stream 14, as well as feed stream 4 (optionally after the addition of a separate benzene feed stream 12b) may be heated to a desired temperature in this range using a heat exchanger (not shown).

In the embodiment illustrated in FIG. 1, therefore, a first transalkylation reaction zone through which the combined feed stream 14 (comprising the second transalkylation feed stream 6, enriched in TIPB) is passed, comprises both of the catalyst beds 50, 60. The first transalkylation feed stream 4, enriched in DIPB is fed to a second transalkylation reaction zone comprising only the second zeolitic catalyst bed 60 of the stacked, 2-bed transalkylation reactor 200 employing both beds 50, 60 of zeolitic catalyst. Optionally, an additional benzene stream 12b may be combined with the first transalkylation feed stream 6 enriched in TIPB, upstream of transalkylation reactor 200. In the arrangement of first and second transalkylation zones in the embodiment illustrated in FIG. 1, the first zeolitic catalyst bed 50 preferably comprises Y zeolite (e.g., the modified Y zeolite known as Y-85) and the second zeolitic catalyst bed 60 comprises beta zeolite. The use of such zeolitic transalkylation catalyst beds advantageously reduces the formation of byproducts and particularly ethylbenzene, as discussed above.

By using separate transalkylation reaction zones (i.e., a first zone comprising two zeolitic catalyst beds 50, 60 and a second zone comprising only one of the two beds) the reaction zones can be better tailored to the different transalkylation feed streams 4, 6, compared to the case where only a single transalkylation feed stream is generated in the upstream diisopropylbenzene column 100. This allows for improved conversion to, and/or selectivity for, the desired transalkylation reaction that produces additional cumene in the transalkylation reaction zone effluent 18. This effluent 18 is then advantageously combined with an effluent from an alkylation reaction zone used to alkylate benzene with propylene to produce cumene. These effluents are optionally combined after the removal of light components such as propane and/or water from this alkylation reaction zone effluent using distillation. The combined effluents are then generally passed to the product separation section of the combination alkylation zone/transalkylation zone cumene production process as described previously.

FIG. 2 illustrates an alternate, representative method for transalkylating the hydrocarbon feed stream 2, as described with respect to the embodiment illustrated in FIG. 1. Again, the hydrocarbon feed stream 2 is fractionated in diisopropylbenzene column 100 into two separate transalkylation feed streams 4, 6 enriched in DIPB and TIPB, respectively. However, these feed streams 4, 6 are sent to separate transalkylation reactors 200a, 200b. Benzene stream 12a is combined with the second transalkylation feed stream 6, enriched in TIPB to provide combined feed stream 14a that is passed to the inlet of first transalkylation reactor 200a, such that the first transalkylation reaction zone comprises only the first bed 50 of zeolitic catalyst, preferably comprising Y zeolite. A second transalkylation reaction zone comprising only the second bed 60 of zeolitic catalyst, preferably comprising beta zeolite, is used to react benzene stream 12b and first transalkylation feed stream 4, enriched in DIPB.

In the embodiment illustrated in FIG. 2, benzene stream 12a is preferably combined with the transalkylation feed stream 6 enriched in TIPB to provide a benzene:TIPB molar ratio from about 5:1 to about 25:1 at the inlet of the first transalkylation reactor 200a. This preferred range of molar benzene:TIPB ratios is the same as a preferred range of molar benzene:DIPB ratios at the inlet of the second transalkylation reactor 200b. The temperatures of the combined feed streams 14a, 14b at the inlets of their respective transalkylation reactors 200a, 200b are preferably from about 100° C. (212° F.) to about 200° C. (392° F.) in each case. In the embodiment illustrated in FIG. 2, the separate transalkylation effluent streams 18a, 18b may then both be combined with the effluent from an alkylation reaction zone as discussed above, if the transalkylation reaction zones 200a, 200b are to be integrated with an alkylation reaction zone in an overall, combined process for cumene production.

Thus, according to the embodiments of FIGS. 1 and 2, the transalkylation reaction zone effluent streams (stream 18 in FIG. 1 and streams 18a, 18b in FIG. 2) can contain relatively fewer byproducts of the transalkylation reaction, compared to cases where separate transalkylation feed streams enriched in different polyalkylated aromatic transalkylation agents are not obtained (e.g., via fractionation). Byproduct reduction is therefore a consequence of using different transalkylation reaction zones for the different transalkylation feed streams. For example, separate catalyst beds, such as beds 50, 60 shown in the embodiments illustrated in FIGS. 1 and 2, will generally comprise different catalysts that are tailored to each of the separate transalkylation feed streams 4, 6. It is also recognized, however, that even if the catalyst beds 50, 60 contain the same catalyst, it is still possible for other conditions, such as temperature, residence time, and/or benzene:polyalkylated aromatic compound molar ratio, (e.g., in the case of the catalyst beds being in a common reactor, as in the embodiment illustrated in FIG. 1) to provide different transalkylation reaction zones when the transalkylation feed streams are fed to different points of the reactor.

In the case separate reactors, as used in the embodiment illustrated in FIG. 2, different catalyst types, temperatures, pressures, residence times, molar ratios, and/or other parameters can be used individually or in combination to provide the different transalkylation reaction zones in order to reduce transalkylation zone byproduct formation. The use of conventional pressure, flow, and temperature control systems (e.g., including combined feed heaters or heat exchangers), which are not shown in FIGS. 1 and 2, can be used to maintain desired conditions in the different transalkylation reaction zones to reduce byproduct formation. The reduction of byproduct ethylbenzene, for example, is of important commercial interest due to its having a similar relative volatility to that of cumene, causing it to co-boil with cumene product in the cumene column, thereby reducing cumene product purity.

It will be appreciated that the embodiment illustrated in FIG. 2, utilizing separate transalkylation reactors, allows independent control of benzene flow to each transalkylation reaction zone. The advantages and disadvantages associated with any particular flowscheme, in terms of the degree to which reaction zone conditions may be controlled as well as other parameters, for example, benzene usage and catalyst requirements, will be apparent to those having skill in the art and knowledge gained from the present disclosure. It will also be appreciated that various changes can be made in the above processes without departing from the scope of the present disclosure. Mechanisms used to explain theoretical or observed phenomena or results, shall be interpreted as illustrative only and not limiting in any way the scope of the appended claims.

What is claimed is:

1. A method for transalkylating a hydrocarbon feed stream comprising first and second polyalkylated aromatic transalkylation agents, the method comprising:
    (a) separating the hydrocarbon feed stream to provide a first transalkylation feed stream enriched in the first polyalkylated aromatic transalkylation agent and a second transalkylation feed stream enriched in the second polyalkylated aromatic transalkylation agent,
    wherein the first and second polyalkylated aromatic transalkylation agents are diisopropvlbenzene (DIPB) and triisopropvlbenzene (TIPB) or the first and second polyalkylated aromatic transalkylation agents are diethylbenzene (DEB) and triethylbenzene (TEB), and the second polyalkylated aromatic transalkylation agent is present in the hydrocarbon feed stream in an amount of less than about 10% by weight;
    (b) processing the second transalkylation feed stream through a first zeolite catalyst bed comprising Y zeolite or UZM-8 zeolite, and subsequently a second zeolite catalyst bed comprising beta zeolite, downstream of the first zeolite bed, the first and the second zeolite catalyst bed forming the first transalkylation reaction zone;
    c) passing the first transalkylation feed stream to the second transalkylation reaction zone, the second transalkylation reaction zone comprising the second zeolite catalyst bed; and
    d) producing a second transalkylation reaction zone effluent having additional cumene.

2. The method of claim 1, wherein the different transalkylation reaction zones are within a common reactor.

3. The method of claim 1, wherein the different transalkylation reaction zones are within separate reactors.

4. The method of claim 1, wherein the hydrocarbon stream comprises a process stream of a product separation section in a cumene production process.

5. The method of claim 4, wherein the hydrocarbon feed stream is obtained from distillation to recover a cumene product stream as a lower boiling fraction.

6. The method of claim 1, wherein the hydrocarbon feed stream comprises a process stream of a product separation section in an ethylbenzene production process.

7. The method of claim 6, wherein the hydrocarbon feed stream is obtained from distillation to recover an ethylbenzene product stream as a lower boiling fraction.

8. The method of claim 1, wherein step (b) provides at least one transalkylation reaction zone effluent stream enriched in an alkylaromatic product, and the method further comprises combining the at least one transalkylation reaction zone effluent with an alkylation reactor effluent stream.

9. The method of claim 8, wherein the at least one transalkylation reactor effluent stream and the alkylation reactor effluent stream are combined prior to or during distillation to enrich a lower boiling fraction in an aromatic alkylation substrate.

10. The method of claim 9, wherein the aromatic alkylation substrate is benzene.

11. The method of claim 1 wherein the first zeolite bed consists essentially of Y zeolite and the second zeolite bed consists essentially of beta zeolite.

12. A method for transalkylating a hydrocarbon feed stream comprising diisopropylbenzene (DIPB) and triisopropylbenzene (TIPB), the method comprising:
    (a) fractionating the hydrocarbon feed stream to provide a transalkylation feed stream enriched in DIPB and a transalkylation feed stream enriched in TIPB; and
    (b) feeding benzene and the transalkylation feed stream enriched in TIPB to a first transalkylation reaction zone comprising beds of first and second zeolitic catalysts, wherein the first zeolitic catalyst comprises Y zeolite or UZM-8 zeolite and the second zeolitic catalyst comprises beta zeolite; and
    (c) feeding the transalkylation feed stream enriched in DIPB to a second transalkylation reaction zone comprising the bed of the second zeolitic catalyst.

13. The method of claim 12, wherein the transalkylation feed stream enriched in DIPB and the transalkylation feed stream enriched in TIPB are lower and higher boiling side draw streams, respectively, of a fractionation column in a product recovery section of a cumene production process.

14. The method of claim 12, wherein, in step (b), benzene and the transalkylation feed stream enriched in TIPB are present at an inlet of the first transalkylation reaction zone at a benzene : TIPB molar ratio from about 5:1 to about 100:1 and at a temperature from about 100° C. (212° F.) to about 200° C. (392° F.).

15. A method for transalkylating a hydrocarbon feed stream comprising diisopropylbenzene (DIPB) and triisopropylbenzene (TIPB), the method comprising:
    (a) fractionating the hydrocarbon feed stream to provide a transalkylation feed stream enriched in DIPB and a transalkylation feed stream enriched in TIPB, wherein the transalkylation feed stream enriched in TIPB further comprises DIPB; and
    (b) reacting benzene with the transalkylation feed stream enriched in TIPB in a first transalkylation reaction zone, the first transalkylation reaction zone comprising a first bed comprising a Y zeolite or UZM-8 zeolite and a second bed comprising beta zeolite, the second bed downstream of the first bed, wherein the TIPB reacts with the benzene in the first bed to form cumene, and wherein the DIPB in the transalkylation feed stream enriched in TIPB reacts with the benzene in the second bed to form cumene; and
    (c) reacting benzene with the transalkylation feed stream enriched in DIPB in a second transalkylation reaction zone, the second transalkylation reaction zone comprising a bed comprising beta zeolite.

16. The method of claim 15, wherein, in step (b), benzene and the transalkylation feed stream enriched in TIPB are present at an inlet of the first transalkylation reactor at a benzene : TIPB molar ratio from about 2:1 to about 25:1 and at a temperature from about 100° C. (212° F.) to about 200° C. (392° F.) and wherein, in step (c), benzene and the transalkylation feed stream enriched in DIPB are present at an inlet of the second transalkylation reactor at a benzene : DIPB molar ratio from about 2:1 to about 25:1 and at a temperature from about 100° C. (212° F.) to about 200° C. (392° F.)

* * * * *